(12) United States Patent
Walter et al.

(10) Patent No.: US 6,699,166 B2
(45) Date of Patent: Mar. 2, 2004

(54) GEOMETRIC FOLDING OF A WEB USED IN A DISPOSABLE ABSORBENT ARTICLE

(75) Inventors: John Walter, Renfrew, PA (US); Troy Delzer, Butler, PA (US)

(73) Assignee: Paragon Trade Brands, Inc., Norcross, GA (US)

( * ) Notice: Subject to any disclaimer, the term of this patent is extended or adjusted under 35 U.S.C. 154(b) by 156 days.

(21) Appl. No.: 10/095,096

(22) Filed: Mar. 12, 2002

(65) Prior Publication Data

US 2003/0176266 A1 Sep. 18, 2003

(51) Int. Cl.[7] .................................................. B31F 7/00
(52) U.S. Cl. ....................... 493/446; 493/447; 493/455; 493/456; 493/434; 493/427
(58) Field of Search ................................ 493/431, 434, 493/416, 424, 423, 427, 442, 446, 447, 455, 456

(56) References Cited

U.S. PATENT DOCUMENTS

| | | | | |
|---|---|---|---|---|
| 3,608,889 A | * | 9/1971 | Woessner et al. | 493/360 |
| 3,685,820 A | * | 8/1972 | Surbrook | 493/360 |
| 3,799,536 A | * | 3/1974 | Gregoire | 493/359 |
| 4,022,457 A | * | 5/1977 | Marin et al. | 493/399 |
| 4,558,581 A | * | 12/1985 | Goulstone et al. | 72/176 |
| 5,873,809 A | * | 2/1999 | Kempster et al. | 493/464 |
| 6,557,466 B2 | * | 5/2003 | Codde et al. | 101/216 |
| 6,592,699 B1 | * | 7/2003 | Mehta et al. | 156/227 |

* cited by examiner

*Primary Examiner*—Eugene Kim
*Assistant Examiner*—Sameh H. Tawfik
(74) *Attorney, Agent, or Firm*—Hunton & Williams

(57) ABSTRACT

A device is provided for folding a material web traveling in a machine direction. The device has a folding portion having a leading edge, a breaking wing attached to the folding portion, the breaking wing having a breaking edge, and a roller rotatably attached to the breaking wing and having a surface and a rotational axis. The rotational axis is along a transverse direction, the transverse direction being substantially perpendicular to the machine direction. The roller is for supporting a roller portion of the material web as the material web is fed to the folding portion, and the breaking wing is for supporting a wing portion of the material web as the material web is fed to the folding portion. The surface of the roller is positioned in the transverse direction at a first angle relative to the rotational axis, the breaking edge of the breaking wing is positioned in the transverse direction at a second angle relative to the rotational axis, and the first angle is different from the second angle.

55 Claims, 8 Drawing Sheets

GEOMETRIC FOLDING OF A WEB USED IN A DISPOSABLE ABSORBENT ARTICLE

FIELD OF THE INVENTION

The present invention generally relates to folding machinery. In particular, it relates to folding of web materials used in disposable absorbent articles.

BACKGROUND OF THE INVENTION

Fabrics, such as textiles, woven materials and nonwoven materials constructed from natural or synthetic fibers, may be processed into garments or other assemblies by feeding them through processing lines. These processing lines may operate non-stop or with few interruptions. In many instances when a product being made in the processing line includes fabric or other sheet-like material, these materials are stored in roll form and fed into the line as a continuously moving web of material. When the roll runs out of fabric, a substitute roll may be inserted into the line with or without interrupting the activity of the line. The web may be processed in any number of ways, such as by folding, pinching, bonding, gluing, compressing, sewing, cutting, and the like. In many cases it is preferred that these operations be performed in the machine direction, that is, done in the direction that the material is moving without interrupting the constant flow of fabric along the line.

SUMMARY OF THE INVENTION

The invention provides a device for folding a material web traveling in a machine direction. The device has a folding portion having a leading edge, a breaking wing attached to the folding portion, the breaking wing having a breaking edge, and a roller rotatably attached to the breaking wing and having a surface and a rotational axis. The rotational axis is along a transverse direction, the transverse direction being substantially perpendicular to the machine direction. The roller is for supporting a roller portion of the material web as the material web is fed to the folding portion, and the breaking wing is for supporting a wing portion of the material web as the material web is fed to the folding portion. The surface of the roller is positioned in the transverse direction at a first angle relative to the rotational axis, the breaking edge of the breaking wing is positioned in the transverse direction at a second angle relative to the rotational axis, and the first angle is different from the second angle.

The invention also provides a method of folding a material web traveling in a machine direction. The method includes feeding a roller portion of the material web onto a roller such that the roller portion of the material web is supported by the roller, feeding a wing portion of the material web onto a breaking wing such that the wing portion of the material web is supported by the breaking wing, and feeding the roller portion and the wing portion of the material web to a folding portion having a leading edge. The breaking wing has a breaking edge, the roller is rotatably attached to the breaking wing and has a surface and a rotational axis along a transverse direction, the transverse direction being substantially perpendicular to the machine direction. The surface of the roller is positioned in the transverse direction at a first angle relative to the rotational axis, the breaking edge of the breaking wing is positioned in the transverse direction at a second angle relative to the rotational axis, and the first angle is different from the second angle.

DETAILED DESCRIPTION OF THE PREFERRED EMBODIMENTS

Figure 1:
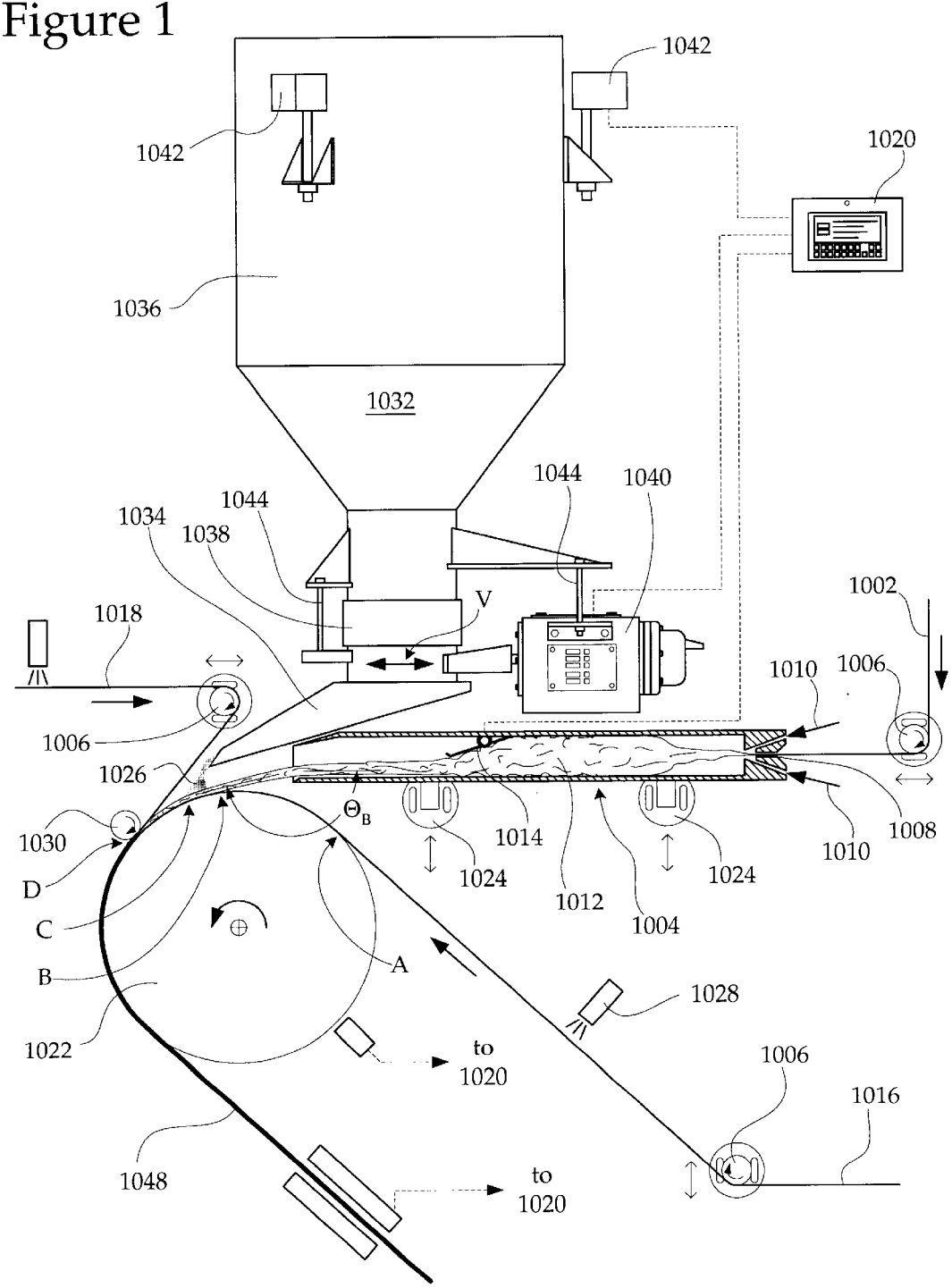
FIG. 1 is a side view of an apparatus for dry forming composite cores.

As understood herein, "processing line" or "line" refers to any manufacturing or assembly line. Such processing lines may operate substantially non-stop, and may move in substantially one direction, or may operate in several directions. Supplies of material may be fed into the line, from any direction, as a continuous supply, or as an intermittent supply. The material fed into the line is generally processed, such as by cutting, joining, folding or stacking the material at various processing stations. Each processing station may process the material in one or more ways. The present invention may be used with any processing line, and the following description is not intended to limit the scope of the application of the invention.

The "machine direction," as used herein, is the primary direction in which material is traveling through the processing line at any given point. The material moving through the processing line generally originates from the "upstream" direction and moves in the "downstream" direction as it is processed. A "forward" or "foremost" portion of a part of the invention is located in the upstream direction, and a "rearward" or "rearmost" portion of a part is in the downstream direction.

As used herein, "fabric" or "material" refers to any woven cloth, nonwoven material, foam, mesh, film, paper, thin plastics and elastics, and the like. In addition, "fabric" or "material" may also refer to any substantially flat material (i.e., having a compressed thickness of less than about one quarter of the overall width or length of the finished product). A "fabric" or "material" may also be an aggregation or laminate of the above materials. A "fabric web", "material web" or "web" is a substantially continuous supply of fabric or material that may be fed into a processing line. The web may be conveyed along the line by any means known in the art, such as by pinch rollers, vacuum drums, foraminous vacuum belts, and the like.

As used herein, the terms "absorbent garment" and "absorbent article" refer to devices that absorb and contain body fluids and other body exudates. More specifically, these terms refer to garments that are placed against or in proximity to the body of a wearer to absorb and contain the various exudates discharged from the body. A non-exhaustive list of examples of absorbent garments includes diapers, diaper covers, disposable diapers, training pants, feminine hygiene products and adult incontinence products. Such garments may be intended to be discarded or partially discarded after a single use ("disposable" garments). Such garments may comprise essentially a single inseparable structure ("unitary" garments), or they may comprise replaceable inserts or other interchangeable parts. The present invention may be used with all of the foregoing classes of absorbent garments, without limitation, whether disposable or otherwise.

Throughout this description, the expressions "upper layer," "lower layer," "above" and "below," which refer to the various components included in the absorbent core units of the invention (including the layers surrounding the absorbent core units) are used merely to describe the spatial relationship between the respective components. The upper layer or component "above" the other component need not always remain vertically above the core or component, and the lower layer or component "below" the other component need not always remain vertically below the core or component. Indeed, embodiments of the invention include various configurations whereby the core is folded in such a manner that the upper layer ultimately becomes the vertically highest and vertically lowest layer at the same time. Other configurations are contemplated within the context of the present invention.

The term "component" can refer, but is not limited, to designated selected regions, such as edges, corners, sides or the like; structural members, such as elastic strips, absorbent pads, stretchable layers or panels, layers of material, or the like; or a graphic. The term "graphic" can refer, but is not limited, to any design, pattern, indicia or the like.

Throughout this description, the term "disposed" and the expressions "disposed on," "disposing on," "disposed in," "disposed between" and variations thereof (e.g., a description of the article being "disposed" is interposed between the words "disposed" and "on") are intended to mean that one element can be integral with another element, or that one element can be a separate structure bonded to or placed with or placed near another element. Thus, a component that is "disposed on" an element of the absorbent garment can be formed or applied directly or indirectly to a surface of the element, formed or applied between layers of a multiple layer element, formed or applied to a substrate that is placed with or near the element, formed or applied within a layer of the element or another substrate, or other variations or combinations thereof.

Absorbent garments and diapers may have a number of different constructions and configurations. In each of these, it generally is the case that an absorbent core is disposed between a liquid pervious, body-facing topsheet, and a liquid impervious, exterior facing backsheet. In some cases, one or both of the topsheet and backsheet may be shaped to form a pant-like garment. In other cases, the topsheet, backsheet and absorbent core may be formed as a discrete assembly that is placed on a main chassis and the chassis is shaped to form a pant-like garment. The garment may be provided to the consumer in the fully assembled pant-like shape, or may be partially pant-like and require the consumer to take the final steps necessary to form the final pant-like shape. In the case of training pant-type garments and most adult incontinent products, the garment is provided fully formed with factory-made side seams and the garment is donned by pulling it up the wearer's legs. In the case of diapers, a caregiver usually wraps the diaper around the wearer's waist and joins the side seams manually by attaching one or more adhesive or mechanical tabs, thereby forming a pant-like structure.

The absorbent core preferably comprises particles of super absorbent polymer (SAP) distributed within a fibrous structure. Additional fibrous or particulate additives may be disposed within the absorbent core to add to the core's strength and SAP efficiency or to otherwise enhance the performance of the garment. The absorbent core may be partially or wholly surrounded by a tissue layer and other additional layers may be added to provide further benefits.

The absorbent core is preferably formed using a dry process. Dry processes have numerous benefits over wet processes. For example, in wet processes, the core material is typically immersed in a fluid having superabsorbent particles mixed or suspended therein, and the core material may require additional drying steps and other steps that add to the complexity and cost of the core forming process. In addition, wet processes often require the absorbent core to be manufactured off of the main assembly line. Dry processes typically have lower operating costs than wet processes because the equipment used in dry processes is typically less complex and can run at higher line speeds. Further, dry forming processes may often be adapted for use directly on the line of conventional diaper machines. A dry forming process is preferable that manufactures absorbent cores having high concentrations of SAP and relatively low basis weights, while overcoming or avoiding the deficiencies of known dry forming processes and machines.

Referring now to FIG. 1, an apparatus and method for dry forming composite cores is shown. A tow supply 1002, which may be unopened or partially opened, is provided along a first path to enter a forming jet assembly 1004. The supply of tow may comprise any material that is desired to be used as the fibrous structure of the garment's absorbent core and is suitable for use in the process described herein. Those skilled in the art will appreciate that if fibers, fluff, or pulp other than tow fibers are used, forming jet assembly 1004 would be replaced by a suitable fiber or fluff forming apparatus, as are well known in the art. A preferred material for the tow supply 1002 is a supply of cellulose acetate having a basis weight of about 50 g/m$^2$ to about 100 g/m$^2$, and more preferably of about 76 g/m$^2$. The tension, speed and path of the tow supply 1002 may be adjusted by one or more movable pulleys 1006, guides (not shown) and/or festoons (not shown), as are known in the art.

The tow supply 1002 enters the forming jet assembly 1004 and is opened in preparation for being incorporated into absorbent cores. The forming jet assembly 1004 comprises a tow inlet 1008 at one end into which the tow supply 1002 is fed. One or more high velocity jets 1010 of air or other gas are projected into the forming jet assembly to impinge upon the tow supply 1002 to thereby separate the fibers and "bloom" or open the tow. Preferably, two jets 1010 are used and each jet 1010 is located proximal to the tow inlet 1008 and on opposite sides of the tow supply 1002. Each of the jets 1010 preferably comprises a flow of air moving at about 17.5 cubic feet per minute through a slit-shaped port that has a length of about 3.94 inches and a width of about 0.003 inches. Similar devices for opening tow are known in the art, and disclosed, for example, in U.S. Pat. No. 5,331,976 to St. Pierre, which is incorporated herein by reference in its entirety and in a manner consistent with the present invention. Other devices and procedures for opening the tow supply 1002 may also be used, as will be understood by those skilled in the art.

The opened or "bloomed" tow 1012 accumulates within the forming jet assembly 1004 as it is being used, and the amount of opened tow 1012 being consumed may be measured by a level meter 1014 (also known as a "dancer"). The level meter 1014 may be any suitable electromechanical, optical, or other type of device capable of measuring the amount of opened tow 1012 being consumed. In a preferred embodiment, the level meter 1014 is a plate that is pivotally attached to a rotary position sensor (such as a commonly known variable resistance or potential device). As the level of opened tow 1012 increases or decreases, the plate pivots up and down, thereby changing the output of the rotary position sensor. The level meter 1014 can be used as part of a closed-loop feedback algorithm or an open-loop algorithm to meter the rate at which the tow supply 1002 is fed into the forming jet assembly 1004, and may be integrated into a control system 1020.

The control system 1020 may comprise any electrical control apparatus that may be configured to control one or more variables based on the measurement of one or more inputs. Although the control system 1020 is referred to herein in the singular, it should be understood that a number of independent control systems 1020 may be used for various parts of the machinery, and these various systems are referred to collectively herein as a single control system 1020. The control system 1020 may control any number of variables and have any number of inputs, and may use an open-loop or closed-loop algorithm. Exemplary control systems 1020 include programmable logic control (PLC) devices having easily used human machine interfaces, as are known in the art. Of course, the control system 1020 may simply comprise a human operator that monitors the various inputs and adjusts the various system variables.

The opened tow 1012 preferably is pulled out of the forming jet assembly 1004 by a vacuum draw roll 1022, such as a combining drum or a similar drawing device. The opened tow 1012 exits the forming jet assembly 1004 at a tow break angle $\Theta_B$, which may be adjusted by altering the position of the vacuum draw roll 1022 (or similar device), or, more preferably, by adjusting the height and angle of the forming jet assembly 1004 using adjustable mounts 1024. Increasing the tow break angle $\Theta_B$ increases the drag on the opened tow 1012 and thereby increases the amount of stretch that the vacuum draw roll 1022 imparts on the opened tow 1012. Greater stretch reduces the basis weight of the opened tow 1012 that is pulled onto the vacuum draw roll 1022. The tow forming jet 1004 preferably is aligned so that its outlet is tangential to the vacuum draw roll 1022 or slightly above a tangent to the vacuum draw roll 1022. Preferably, the outlet of the tow forming jet 1004 is located at a tangent to the vacuum draw roll 1022 to about 1 inch above a tangent to the vacuum draw roll 1022. More preferably, the outlet of the tow forming jet 1004 is less than about 0.75 inches above a tangent to the vacuum draw roll 1022, and most preferably, the outlet of the tow forming jet 1004 is located less than about 0.5 inches above a tangent to the vacuum draw roll 1022.

The tow forming jet's adjustable mounts 1024 may be fixed in a desired position during machine operation, or may be actively operated by a control system 1020 during operation in response to measurements of the core basis weight or other feedback gathered during operation. Mechanical, electromechanical, pneumatic, hydraulic, or other suitable adjusting devices may be used to actuate the adjustable mounts 1024, such as stepper motors, solenoids and hydraulic or pneumatic pistons or rams, and the like. Alternatively, or in addition, the basis weight of the opened tow 1012 may be adjusted by increasing or decreasing the speed of the vacuum draw roll 1022, with faster speeds generally resulting in a lower basis weight of the opened tow 1012.

After the opened tow 1012 exits the forming jet assembly 1004, a supply of superabsorbent particles 1026 is delivered to the opened tow 1012, and the tow/SAP composite is encased between first and second casing sheet supplies 1016, 1018. Alternatively, the tow/SAP composite may be encased within a fold in a single casing sheet. Preferably, as shown in FIG. 1, the opened tow 1012 is laid onto a first casing sheet supply 1016 before the SAP 1026 is fed to the opened tow 1012 to help contain the SAP 1026 and control the SAP distribution, then the second casing sheet supply 1018 is laid on the tow/SAP composite to form an absorbent core subassembly that may be processed into absorbent garments.

The first and second casing sheet supplies 1016, 1018 encase the opened tow and SAP composite. The first and second casing sheet supplies 1016, 1018 preferably form the first and second tissue layers of the completed garment, but may also form the topsheet and backsheet of the absorbent garment, or any other layers. The first and second casing sheet supplies 1016, 1018 are preferably wider than the opened tow 1012 that forms the absorbent core, and their side portions are preferably sealed to one another by bonding or crimping to prevent release of opened tow 1012 and particles of SAP. The absorbent core composite 1048, comprising the assembly of the first and second casing sheet supplies 1016, 1018 and the opened tow 1012 and SAP 1026 core, may be further processed as it is conveyed through the assembly line for inclusion into absorbent garments. For example, the absorbent core composite 1048 can be severed into individual absorbent cores, and the severed ends may be crimped or bonded to prevent the SAP 1026 from exiting the ends.

In all cases, at least one of the first and second casing sheets 1016, 1018 should be liquid permeable and positioned in the garment to face the wearer's body to allow the flow of fluids into the core. The other casing sheet supply may optionally be liquid impermeable. The liquid impermeability or permeability of either of the casing sheet supplies 1016, 1018 may be provided by chemical or physical treatment, or by the proper selection of materials, as is known in the art. Alternatively, the first and second casing sheets 1016, 1018 may both be formed from a single sheet of material that is folded to encase the opened tow 1012 and SAP 1026.

It may be desirable to apply an adhesive to one or both of the first and second casing sheet supplies 1016, 1018 prior joining them with the opened tow 1012 or tow/SAP combination. For example, it may be preferable for an adhesive to be applied to the entire width of one or both of the casing sheet supplies 1016, 1018 by adhesive applicators 1028 before they are joined with the opened tow 1012 to provide a better bond between the casing sheets 1016, 1018 and the tow/SAP composite. The adhesive may also function to fix a portion of the SAP particles 1026 in place. The supplies casing sheet material 1016, 1018 can be wider than the tow/SAP composite, and adhesive can be applied along the lateral edges of one or both of the casing sheet supplies to join them to one another, thereby sealing in the tow/SAP composite. Other uses of adhesives will be apparent to those skilled in the art based on the teachings provided herein.

A preferred adhesive for these and other embodiments is H2561U hot melt construction adhesive, available from Atofindley of Wauwatosa, Wis. Other suitable adhesives, known in the art, may be used provided they do not excessively impair the desired properties of the casing sheet material, or add excessive stiffness to the absorbent core. For example, other adhesives may include HL-1258 by H. B. Fuller Company of St. Paul, Minn.; Findley 2031 and H2587-01 by Ato Findley Inc. of Wauwatosa, Wis.; and NS34-5665 by National Starch Co. of Bridgewater, N.J. Other adhesives that may be used include 34–578A by National Starch Co. of Bridgewater, N.J. In another preferred embodiment, the adhesive may be selected to impart desired properties to the casing sheet supplies 1016, 1018. For example, an adhesive may be used to render one of the casing sheet supplies 1016, 1018 fluid impervious, opaque, hydrophobic (or hydrophilic), and so on the adhesive may also be water soluble or have other beneficial properties. Adhesive applicators that may be used with the present invention include spray applicators, such as those provided by Nordson Corporation of Westlake, Ohio, or other suitable applicators, as are known in the art.

Still referring to FIG. 1, the absorbent core composite 1048 is assembled in four procedures that take place as the various parts of the assembly are pulled onto the rotating vacuum draw roll 1022. In the first step, which takes place at location A, the first casing sheet supply 1016 is drawn onto the vacuum draw roll 1022. In the second step, at location B, the opened tow 1012 is drawn onto the vacuum draw roll 1022 to overlay the first casing sheet supply 1016 after being pulled out of the forming jet assembly 1004. In the third step, at location C, a supply of SAP 1026 is deposited onto the opened tow 1012 by the vibratory feeder 1032, as described herein. And in the fourth step, at location D, the second casing sheet supply 1018 is brought in to overlie the first casing sheet supply 1016, opened tow 1012 and deposited SAP. Those skilled in the art will appreciate that these steps may be performed using equipment other than that specifically described herein, and may also be performed in various different orders, with some of the steps being rearranged, omitted or combined, or with additional steps being performed. Such variations are generally within the scope of the present invention.

A lay on roll 1030 can be used to press the second casing sheet supply 1018 against the tow/SAP composite and the first casing sheet supply 1016. The lay on roll 1030 helps flatten the core assembly and improves the edge seals between the first and second casing sheet supplies 1016, 1018. The lay on roll 1030 may also be equipped to provide ultrasonic, heat, or other bonds between one or more of the first and second casing sheets 1016, 1018 and the tow/SAP composite. In such an embodiment, the lay on roll 1030 may cooperate with the vacuum draw roll 1022 or other device to create the desired bonds. For example, portions of the lay on roll 1030 may form ultrasonic horns or pressure bonds, while corresponding portions of the vacuum draw roll 1032 form ultrasonic or pressure bonding anvils that, together, form an ultrasonic or pressure bond between the first and second casing sheet supplies 1016, 1018.

The superabsorbent particles preferably are provided by a vibratory feeder 1032. The vibratory feeder 1032 comprises a feed tray 1034 that is attached to and driven by a motor 1040. The motor 1040 vibrates the feed tray 1034, moving it back and forth in the direction of vibration V, as indicated by the double-headed arrow in FIG. 1. The feed tray 1034 is supplied from above by a hopper 1036 by way of a flexible coupling 1038 that helps isolate the hopper 1036 from the movement of the feed tray 1034. The vibratory feeder is preferably suspended on one or more, and most preferably three, scales 1042 that weigh the vibratory feeder 1032 and its contents. The vibratory feeder 1032 is preferably positioned so that none of its moving parts, particularly the motor 1040 and feed tray 1034 strike other parts of the machinery during operation.

The hopper 1036 is preferably selected to provide consistent flow characteristics for a variety of superabsorbent polymers or other particulate and fibrous additives. In particular, it is preferred that the hopper 1036 should flow all of its contents in a regular manner, described as "mass flow," so that few or none of the particles become stuck in the hopper 1036, and do not experience sudden surges in the flow rate. Mass flow is present when essentially all of the material in the hopper is in motion whenever any material is withdrawn. This type of flow pattern is also described as first-in-first-out flow. In order to provide the desired mass flow, the hopper 1036 is preferably designed to avoid "bridging" (i.e., when particles become lodged in the hopper by forming a "bridge" or arch-like structure that resists flowing), and to avoid "ratholing" (i.e., when a column of particles flows through the center of the hopper 1036, but those particles along the walls do not flow). When the hopper 1036 provides mass flow, it is not necessary to provide undesirable external forces, which may damage or redistribute the particles, to shake unmoving particles free. Mass flow may be obtained by providing the hopper 1036 with relatively smooth interior walls and by avoiding the use of shallow flow angles within the hopper 1036. The design may vary depending on the particulate matter or SAP 1026 being held in the hopper 1036, and it may be desirable to test the properties of the material, such as the material's slip angle and angle of repose, to obtain a suitable hopper design. The design of mass flow hoppers is generally known in the art, and a skilled artisan will be able to design a suitable hopper without undue experimentation based on the teachings provided herein.

The hopper preferably has a capacity of about 1.5 ft$^3$ to about 10 ft$^3$, and more preferably about 2.25 ft$^3$ to about 6 ft$^3$, and most preferably about 3 ft$^3$. Also, the hopper 1036 preferably discharges through an outlet having a diameter of about 4 inches to about 12 inches, and more preferably about 5 to about 9 inches, and most preferably about 7 inches. The hopper 1036 may be supplied and refilled with SAP using any device and method known in the art. Preferably, the hopper 1036 is filled by a screw (or "auger") type conveyor that moves SAP from a supply source into the hopper 1036. The design of such hoppers 1036, conveyors and supply sources is known in the art, and a skilled artisan will be able to provide a hopper 1036 for use with the present invention without undue experimentation based on the teachings provided herein.

The vibratory feeder 1032 may be suspended from one or more, and most preferably three, scales 1042 that measure the weight of the vibratory feeder 1032 and its contents. The scales may be used to calculate the amount of SAP 1026 that is being distributed onto the opened tow 1012. Such systems are commonly known as "loss-in-weight" systems, as they continuously measure the reduction in weight of the vibratory feeder 1032 as its contents are being emptied. The conveyors and supply sources that feed into the hopper 1036 may also be suspended on scales so that SAP may be added to the hopper during operation, while still being able to calculate the amount of SAP being deposited onto the opened tow 1012. Preferably, the loss-in-weight measurements of the scales 1042 are used with a closed-loop feedback circuit to control the amount of SAP 1026 that is deposited onto the opened tow 1012. Such a circuit is preferably integrated into a control system 1020 that may control other features and operation of the vibratory feeder 1032 and related devices. The scales 1042 may also be used to determine when it is necessary or desirable to refill the hopper.

The scales 1042 are preferably able to read to an accuracy that allows useful determination of the amount of SAP being deposited onto the opened tow 1012.

A flexible coupling 1038 preferably joins the hopper 1036 to the feed tray 1034. The flexible coupling 1038 is used pass SAP or other additives from the hopper 1036 to the feed tray 1034, while simultaneously isolating the hopper 1036 from the vibratory movement of the feed tray 1034 and motor 1040. The flexible coupling 1038 may comprise any durable flexible material, such as canvas and other cloths, or natural or synthetic rubbers. It is preferred that the flexible coupling does not damp or impede the desired vibrating motion of the feed tray 1034 and motor 1040, and thereby impair the ideal SAP feeding. For example, if the flexible coupling 1038 is too rigid, it will reduce the ability of the motor 1040 to vibrate the feed tray 1034 because it will resist deformation, effectively increasing the mass of the feed tray 1034. Also, if the flexible coupling 1038 is too elastically resilient, it will tend to store energy created in it when the feed tray 1034 and motor 1040 are vibrating, and return this stored energy in an uncontrolled manner (i.e., vibrate on its own) thereby creating additional uncontrolled vibrations in the feed tray 1034 and motor 1040. It also is preferred that the flexible coupling 1038 be as light as possible so as to reduce the inertia that must be overcome by the motor 1040 during operation. In a preferred embodiment, the flexible coupling 1038 comprises a rubber material having a diameter and shape selected to join the outlet of the hopper 1036 with an inlet chute of the feed tray 1034.

The feed tray 1034 and motor 1040 preferably are suspended below the hopper 1036 by flexible mounts 1044 that allow the motor 1040 and feed tray 1034 to move relative to the hopper 1036. The flexible mounts 1044 may comprise rods having flexible or pivoting couplings joining them, at each end, to the hopper 1036, motor 1040 and feed tray 1034. Preferably, the flexible mounts 1044 are designed to convey a minimal amount of vertical movement or vibration to the hopper 1036, which may cause the scales 1042 to read inaccurately. The flexible mounts 1044 may be joined to one or more of the hopper 1036, motor 1040 and feed tray 1034 by a dry or liquid-filled elastomeric bushing or coupling. The design and selection of such vibration- and movement-damping couplings are known in the art, and a skilled artisan will be able to select or produce an appropriate coupling system based on the teachings provided herein.

Embodiments of the invention may be used in conjunction with a processing line that processes nonwoven materials and other materials into absorbent garments. The invention is particularly advantageous for folding webs containing thick materials having a relatively low density such as the dry formed composite cores discussed above. The present invention may also be used with any other type of processing line, as will be evident to those skilled in the art. The invention will be understood to encompass, without limitation, all classes and types of processing lines for processing all types of fabrics for all types of applications, including those described herein.

For clarity, features that appear in more than one Figure have the same reference number in each Figure.

Figure 2:
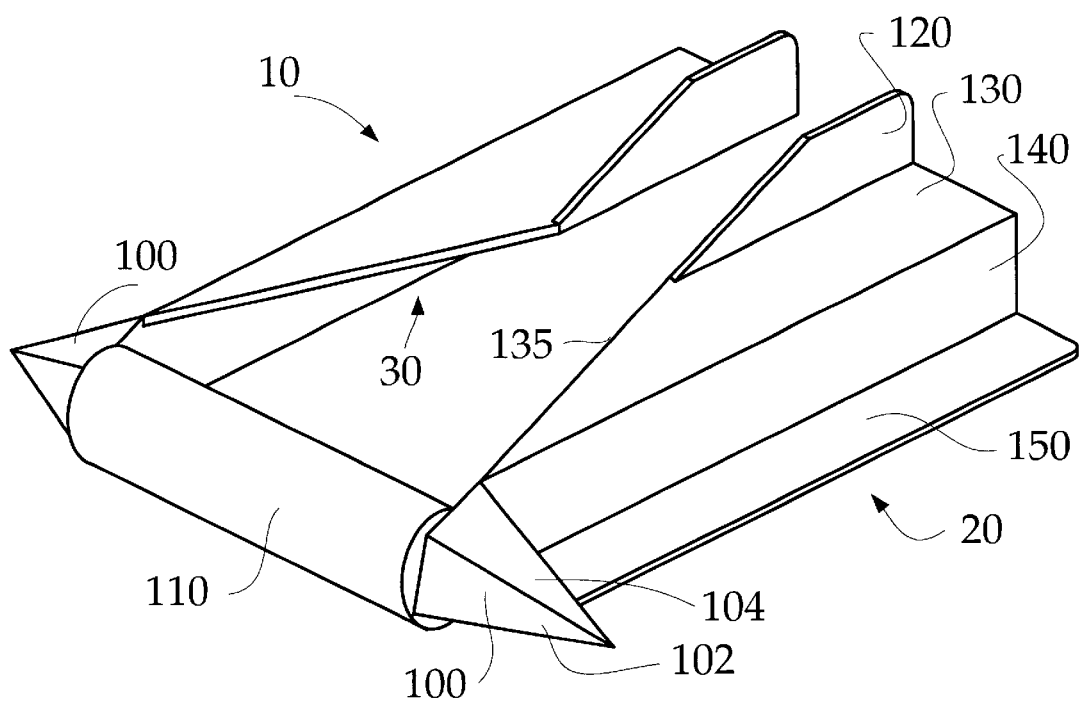
FIG. 2 is an isometric view of an example of an embodiment of the invention.

The invention deals particularly with the portion or portions of a processing line that fold the web. FIG. 2 is an isometric view of an example of one embodiment of the invention. FIG. 2 shows a folder 10 having a first folder side 20 and a second folder side 30. First folder side 20 and second folder side 30 in this example are mirror images of each other. However, in other embodiments, the shape and size of the various elements of the two folder sides may vary such that first folder side 20 and second folder side 30 are not mirror images. First folder side 20 and second folder side 30 are preferably mounted to a frame (not shown) to maintain their position relative to each other. In addition, in this example, roller 110 is positioned between first folder side 20 and second folder side 30. Each of the folder sides 20, 30 have a breaking wing 100 having a lower surface 102 and an upper surface 104. Although breaking wings 100 are shown in this example as having two surfaces, a different number of surfaces may also be provided according to the folding to be performed. In addition, the surface shapes and angles shown in the figures are only examples of some of the appropriate shapes and angles of the invention. Each of the folder sides 20, 30 also include an upper vertical piece 120, a horizontal piece 130, a lower vertical piece 140 and a flange 150. Horizontal piece 130 has a leading edge 135 that assists in the folding performed by folder 10.

Figure 3:
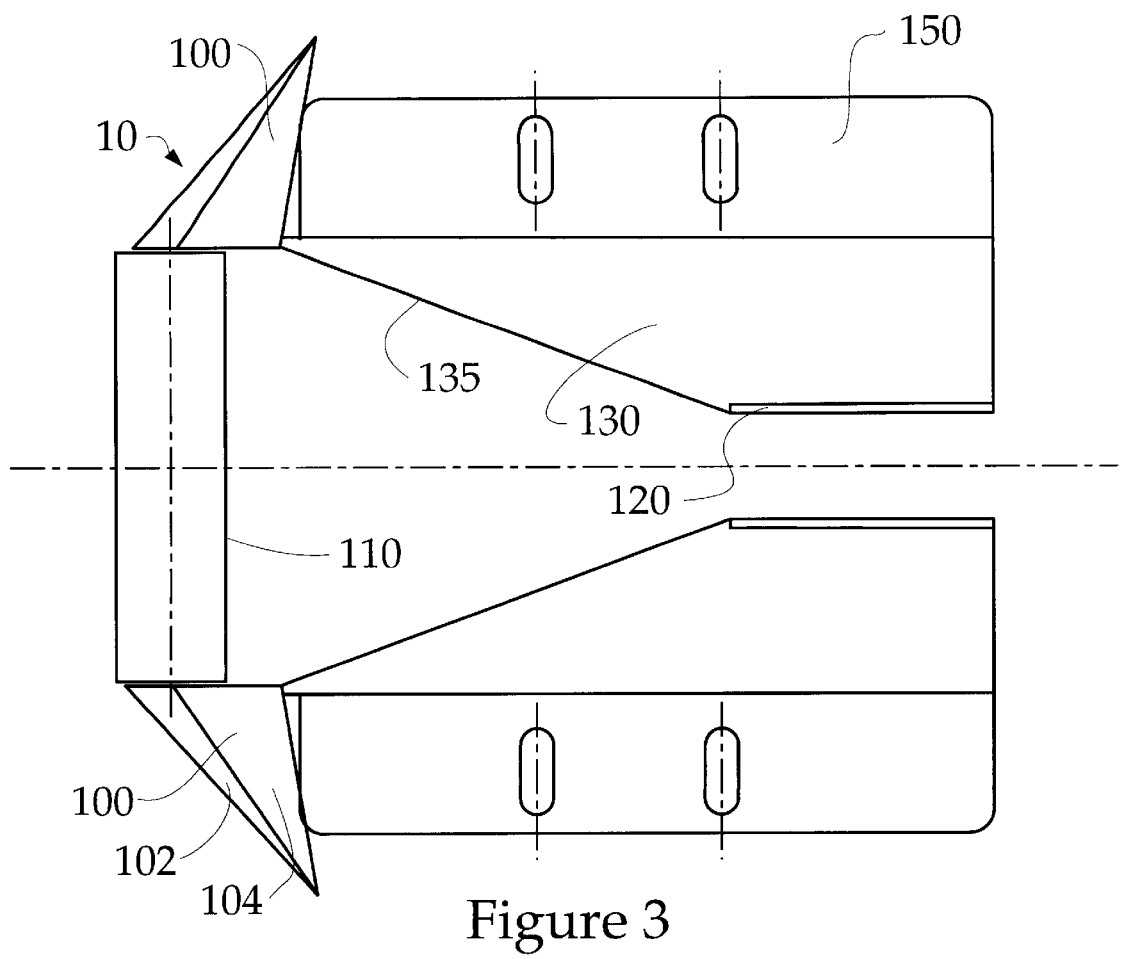
FIG. 3 is a plan view of the embodiment shown in FIG. 2.
Figure 4:
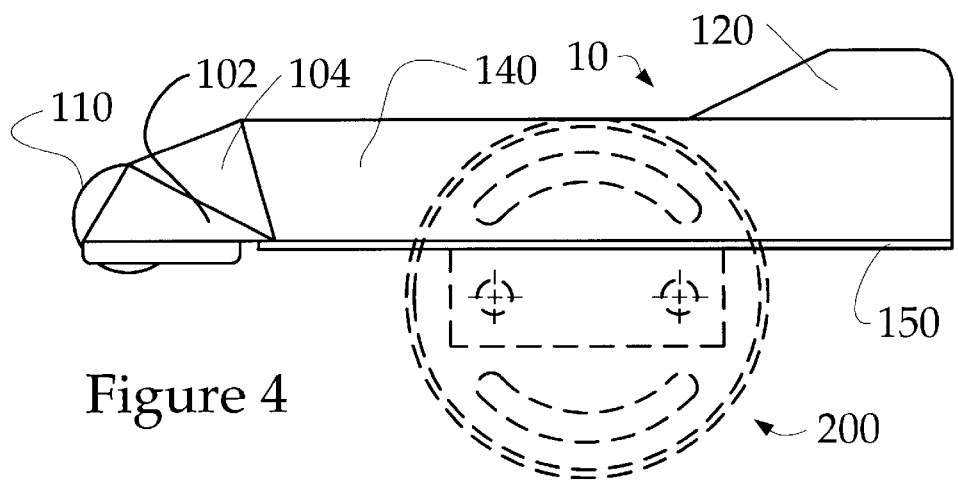
FIG. 4 is a side view of the embodiment shown in FIGS. 2 and 3.
Figure 5:
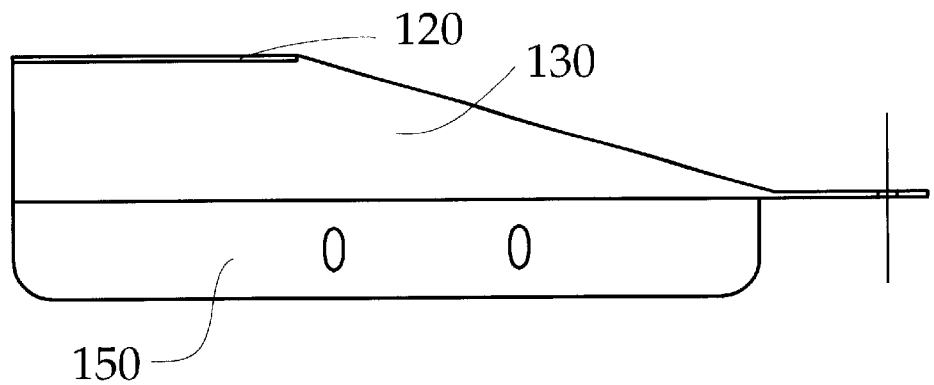
FIG. 5 is a plan view of a piece of an embodiment of the invention.
Figure 6:
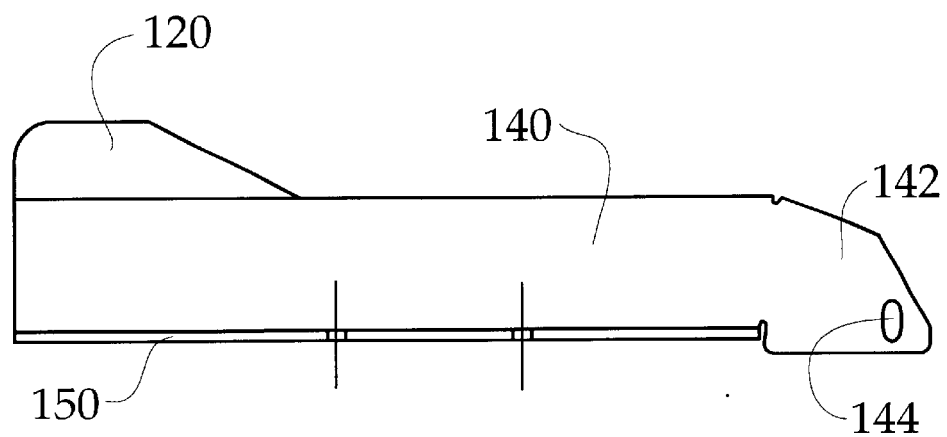
FIG. 6 is a side view of the piece shown in FIG. 5.
Figure 7:
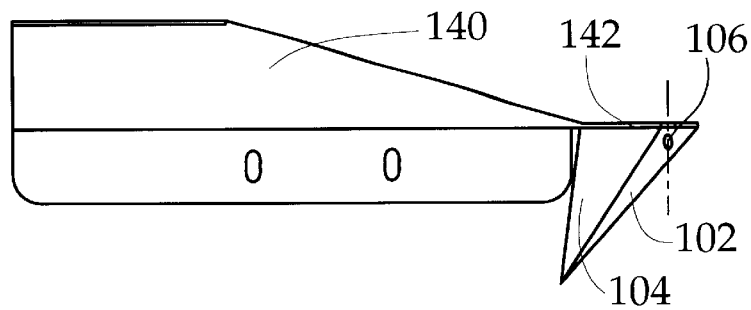
FIG. 7 is a partial plan view of an embodiment of the invention.
Figure 8:
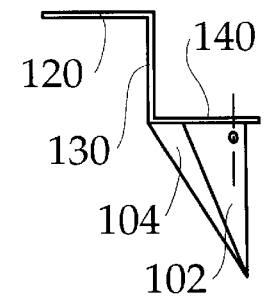
FIG. 8 is an end view of the embodiment shown in FIG. 7.
Figure 9:
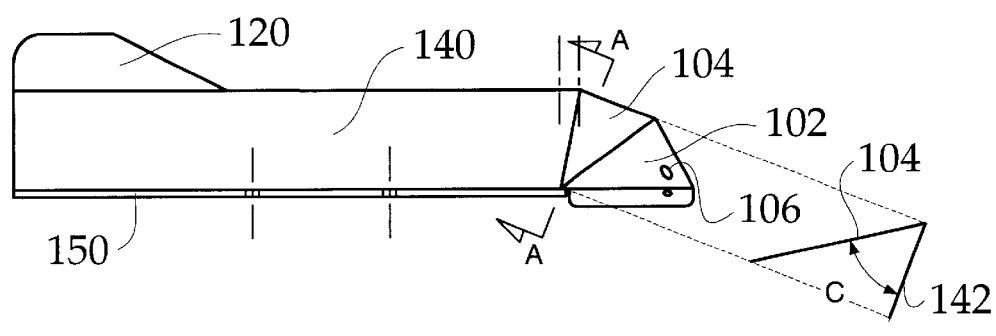
FIG. 9 is a side view of the embodiments shown in embodiments shown in FIGS. 7 and 8.

FIG. 3 shows folder 10 in plan view. FIG. 4 shows a side view of folder 10. Also shown in FIG. 4 as environment, is a rotating mounting structure 200. In this example, first folder side 20 and second folder side 30 are rigidly are mounted to rotating mounting structure 200 and rotating mounting structure 200 would, in turn, be mounted to a frame so that folder 10 can be rotated about a central axis of rotating mounting structure 200. Such mounting permits folder 10 to be positioned at various angles relative to a supply direction of a web to be folded. FIGS. 5 and 6 show a top view and a side view, respectively, of a piece of metal that forms upper vertical piece 120, horizontal piece 130, lower vertical piece 140, and flange 150. Breaking wing 100 is attached to this piece to form each of the folder sides 20, 30. Lower vertical piece 140 includes a wing mounting portion 142 to which the breaking wing 100 is attached. A hole 144 is provided in wing mounting portion 142 in order to accept a spindle on which roller 110 is mounted. FIG. 7 is a plan view showing breaking wing 100 attached to wing mounting portion 142. In this example, a hole 106 is shown in lower surface 102 of breaking wing 100. FIG. 8 is a frontal view of the example shown in FIG. 7. FIG. 9 is a side view of the example shown in FIGS. 7 and 8 with section A—A cut through upper surface 104 of breaking wing 100. Section A—A shows the angle between upper surface 104 and wing mounting portion 142 as C. In a preferred embodiment, angle C equals 57 degrees. However, one skilled in the art could determine other appropriate angles based on the teachings of this disclosure.

Figure 10:
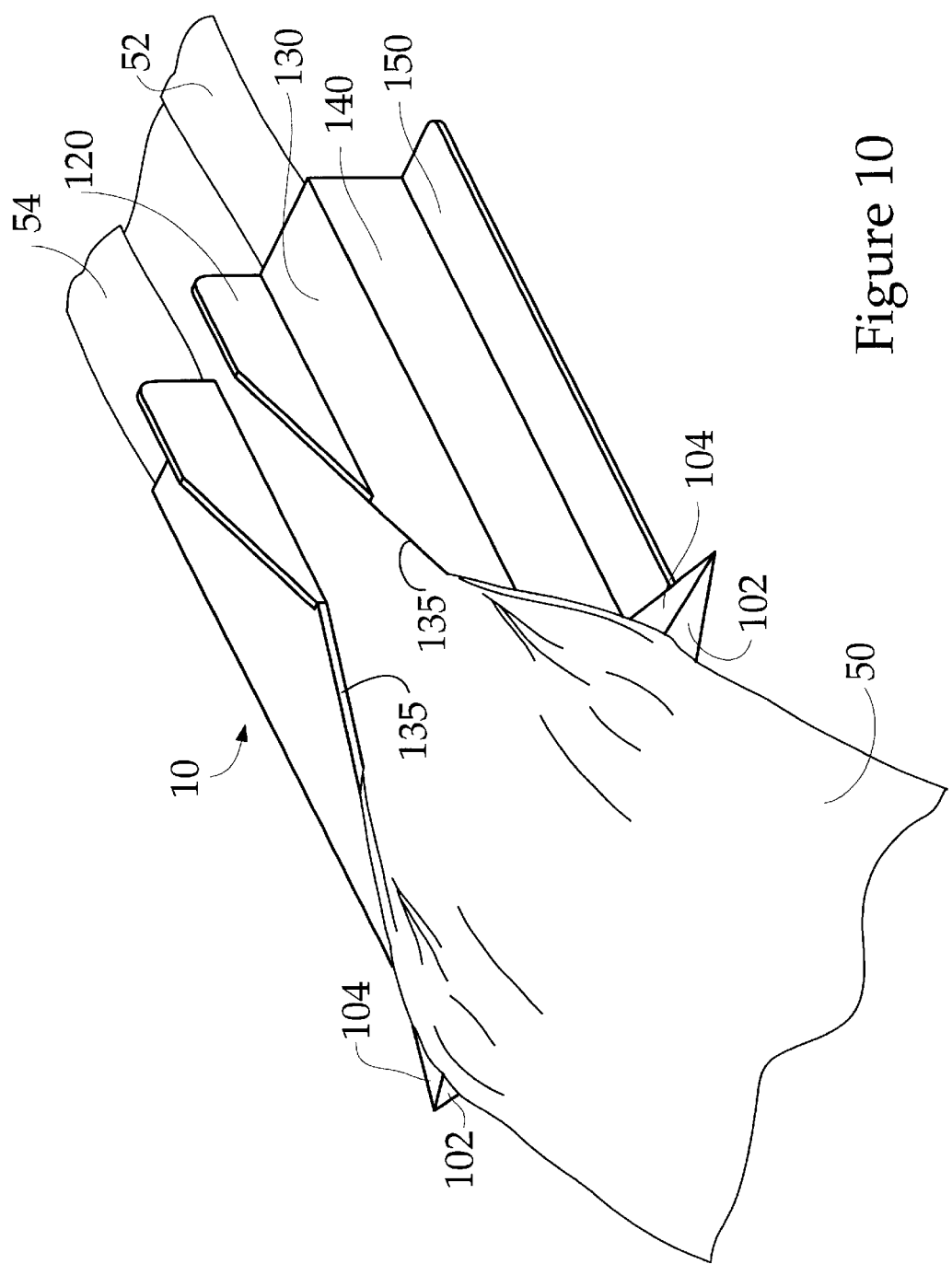
FIG. 10 is an isometric view of the embodiment shown in FIG. 2 in use.

FIG. 10 shows an example of folder 10 in use. Web material 50 is fed, usually pulled, over breaking wings 100 and roller 110 at an upward angle relative to a plane including horizontal pieces 130. Web material 50 is bent downward over breaking wings 100 and roller 110 such that the portion of web material 50 that is on roller 110 is substantially coplanar with horizontal piece 130. In particular embodiments, the portion of the web material that is on roller is not folded by folder 10. As web material 50 passes over breaking wings 100 and advances toward horizontal piece 130, it is folded over upon itself by leading edges 135. Leading edges 135 are preferably set at an angle of approximately 20 degrees to the machine direction. Folded portions 52, 54 of web material 50 then pass underneath horizontal pieces 130 and exit folder 10 to the right in FIG. 10. The shape and angles of lower surfaces 102 and upper surfaces 104 of breaking wings 100 relative to the position and shape of roller 110 in conjunction with tension applied to material web 50 causes material web 50 to bend downward at its out edges to conform to the shape of breaking wings 100. This bending assists the folding of web material 50 as it approaches leading edges 135 of horizontal pieces 130. It is preferable to maintain the same web length across the width of the web. By properly setting the angles of lower surface 102 and upper surface 104 of breaking wings 100 relative to the rotational axis of the roller and taking into account the angle of the leading edges 135, this uniform web length can be maintained. In order to reduce friction between the web material and the various parts of folder 10 and to reduce material build-up, the optimum angles of lower surface 102 and/or upper surface 104 of breaking wings 100 are set in accordance with a preferred height. The preferred height is determined by the thickness of the material web and an estimated factor. The angles of breaking wings 100 are also preferably set to maintain contact between the material web and roller 110 and breaking wings 100. Providing roller 110 instead of a stationary surface reduces friction between web 50 and roller 110. This reduction in friction is particularly important when web material 50 is a thick and/or soft material.

In some embodiments, breaking wings 100 and/or horizontal pieces 130 include a cooling jacket through which water or some other fluid can pass to cool these surfaces. Such cooling can further reduce friction and help reduce glue build up. Cooling can also be provided by other means such as, for example, machining at least horizontal pieces 130 from a block of material such as, for example, aluminum. Horizontal pieces 130 and/or other portions of folder 10 can be attached with fasteners such as, for example, cam latches, to facilitate quick removal for cleaning.

In some embodiments, some or all of the components in contact with the material web are coated with a low friction, high glue release, material such as, for example, Newco/ Impreglon-XPC480/136/857/12, or similar coating.

Figure 11:
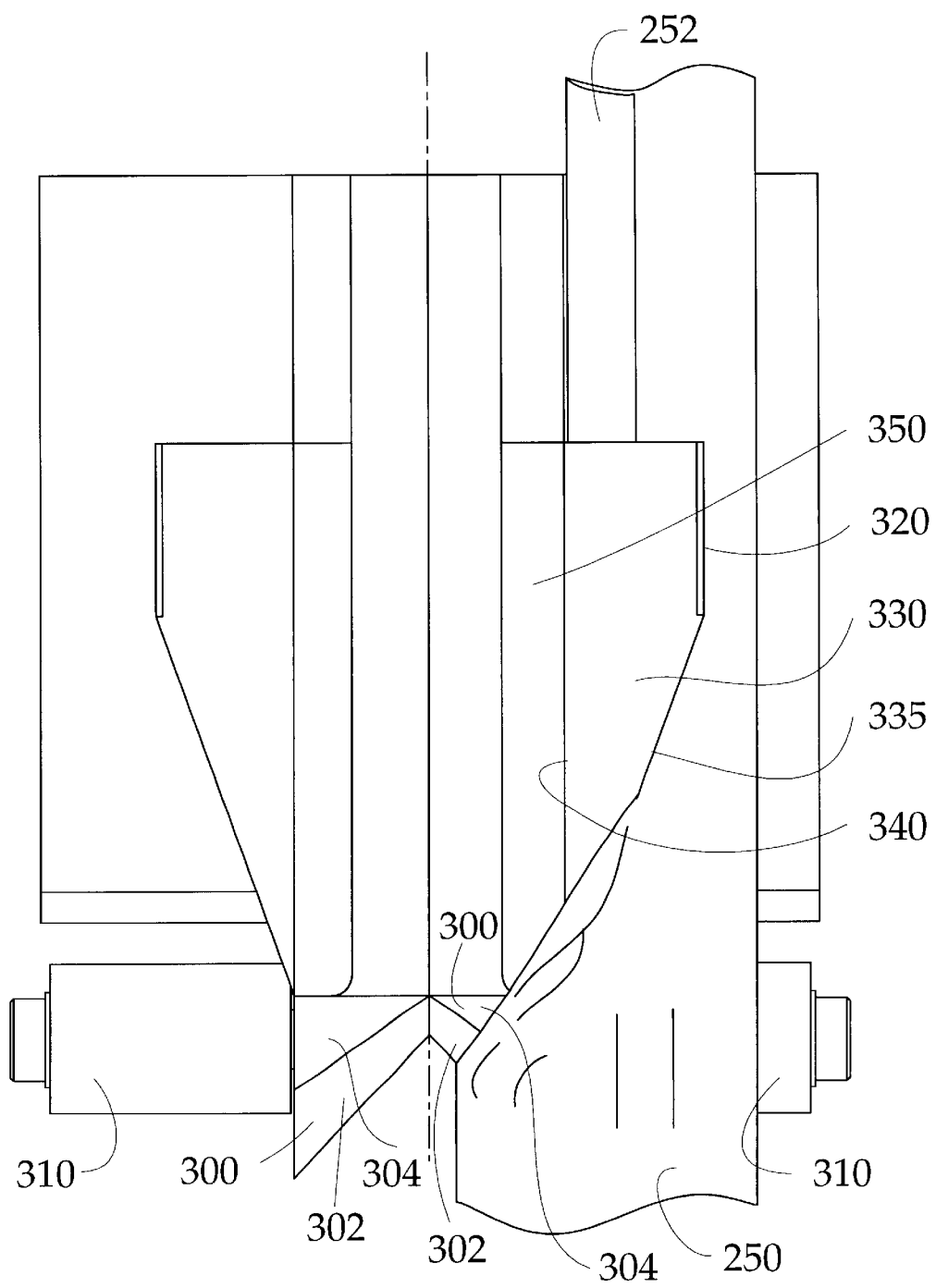
FIG. 11 is a plan view of an example of an embodiment of the invention in use.
Figure 12:
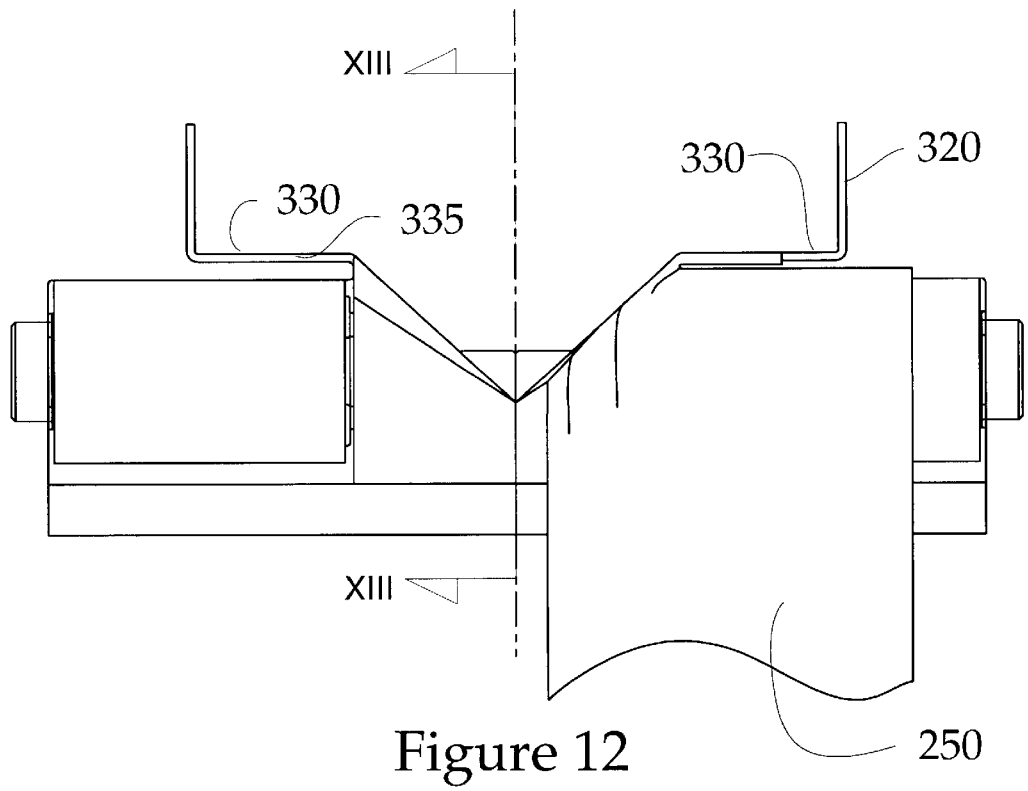
FIG. 12 is a frontal view of the embodiment shown in FIG. 11.
Figure 13:
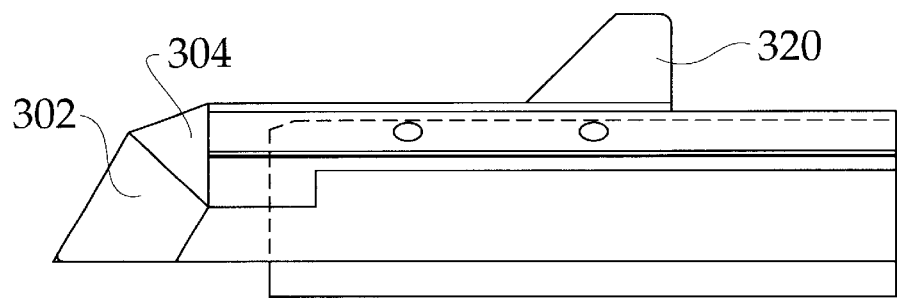
FIG. 13 is a side view of the embodiment shown in FIGS. 11 and 12.

FIGS. 11, 12 and 13 show an embodiment of the invention for folding up to two separate material webs. The configuration of the embodiment shown in FIGS. 11–13 is similar to the embodiment shown in FIG. 2 except that breaking wings 300 (FIG. 11) are adjacent to each other whereas breaking wings 100 (FIG. 2) are on opposite sides of the folder. As shown in FIG. 11, breaking wings 300 have lower surfaces 302 and upper surfaces 304 similar to lower surface 102 and upper surface 104 of breaking wing 100. In this example, each breaking wing 300 has associated with it a roller 310. Each half of the embodiment shown in FIG. 11 has an upper vertical piece 320, a horizontal piece 330, a lower vertical piece 340 and a flange 350. Horizontal piece 330 has a leading edge 335 that is used to fold a web 250. As web 250 is fed into the folder, web 250 is broken over breaking wing 300 and roller 310 and folded over on top of itself by leading edge 335 to produce a folded portion 252.

FIG. 12 is a frontal view of the embodiment shown in FIG. 11 and illustrates the folding of web 250. Although FIGS. 11 and 12 show only one web 250 being folded, it is noted that two separate webs can be folded simultaneously. Further, although FIGS. 11 and 12 show two mirror image halves of the folder, it is noted that a folder may have sides that are not mirror images or have only one side.

FIG. 13 is a sectional view along section line XIII—XIII in FIG. 12.

Many of the features discussed above in reference to the embodiments shown in FIGS. 2–10 also apply to the embodiments shown in FIGS. 11–13. For example, a cooling jacket, or jackets, can be provided as a part of the folder shown in FIGS. 11–13 to assist in cooling, for example, breaking wings 300 or horizontal pieces 330.

Although rollers 110 and 310 are shown as having flat cylindrical surfaces, it is noted that rollers 110 and 310 can have concave or convex surfaces depending on the material being folded and the geometry of other portions of the folder.

While the invention has been described with reference to particular embodiments and examples, those skilled in the art will appreciate that various modifications may be made thereto without significantly departing from the spirit and scope of the invention.

We claim:

1. A device for folding a first material web traveling in a machine direction, the device comprising:

a first folding portion having a leading edge;

a first breaking wing attached to the first folding portion, the first breaking wing having a breaking edge; and a first roller rotatably attached to the first breaking wing and having a surface and a first rotational axis along a first transverse direction, the first transverse direction being substantially perpendicular to the machine direction, wherein the first roller is for supporting a roller portion of the first material web as the first material web is fed to the first folding portion, the first breaking wing is for supporting a wing portion of the first material web as the first material web is fed to the first folding portion, the surface of the first roller is positioned in the first transverse direction at a first angle relative to the first rotational axis, the breaking edge of the first breaking wing is positioned in the first transverse direction at a second angle relative to the first rotational axis, and the first angle is different from the second angle.

2. The device of claim 1, wherein the roller portion of the first material web is to remain unfolded by the device, and the wing portion of the first material web is to be folded by the device.

3. The device of claim 2, wherein the second angle is determined by calculating a preferred height which equals a thickness of the roller portion of the first material web multiplied by a reduced drag/material build-up factor.

4. The device of claim 3, wherein the second angle is such that the roller portion of the first material web remains in contact with the first roller and the wing portion of the first material web remains in contact with the first breaking wing.

5. The device of claim 4, wherein the leading edge of the first folding portion is set at a folding angle relative to the first rotational axis, and the folding angle is approximately 20 degrees.

6. The device of claim 1, wherein the first material web has an underside and an upper side, the first roller is for contacting the underside of the roller portion of the first material web, the first breaking wing is for contacting the underside of the wing portion of the first material web, the leading edge of the first folding portion is for contacting the underside of the wing portion of the first material web, and the first folding portion is for folding the wing portion of the first material web onto the roller portion of the first material web such that the upper side of the wing portion of the first material web contacts the upper side of the roller portion of the first material web.

7. The device of claim 6, wherein the first roller and the first breaking wing are positioned relative to each other such that the roller portion of the first material web can have a different thickness than the wing portion of the first material web.

8. The device of claim 6, wherein the first breaking wing further comprises a cooling jacket through which a cooling fluid flows to cool the first breaking wing.

9. The device of claim 8, wherein the first folding portion further comprises a cooling jacket through which a cooling fluid flows to cool the first folding portion.

10. The device of claim 6, wherein the second material web and the first material web are different webs.

11. The device of claim 10, wherein the first breaking wing further comprises a cooling jacket through which a cooling fluid flows to cool the first breaking wing.

12. The device of claim 11, wherein the first folding portion further comprises a cooling jacket through which a cooling fluid flows to cool the first folding portion.

13. The device of claim 10, wherein the second rotational axis is the first rotational axis.

14. The device of claim 13, wherein the first breaking wing further comprises a cooling jacket through which a cooling fluid flows to cool the first breaking wing.

15. The device of claim 14, wherein the first folding portion further comprises a cooling jacket through which a cooling fluid flows to cool the first folding portion.

16. The device of claim 10, wherein the first roller and the first breaking wing are positioned relative to each other such that the roller portion of the first material web can have a different thickness than the wing portion of the first material web.

17. The device of claim 1, further comprising
a second folding portion having a leading edge;
a second breaking wing attached to the second folding portion,
the second breaking wing having a breaking edge; and
a second roller rotatably attached to the second breaking wing and having a surface and a second rotational axis along a second transverse direction, the second transverse direction being substantially perpendicular to the machine direction,
wherein the second roller is for supporting a roller portion of a second material web as the second material web is fed to the second folding portion,
the second breaking wing is for supporting a wing portion of the second material web as the second material web is fed to the second folding portion,
the surface of the second roller is positioned in the second transverse direction at a third angle relative to the second rotational axis,
the breaking edge of the second breaking wing is positioned in the second transverse direction at a fourth angle relative to the second rotational axis, and
the third angle is different from the fourth angle.

18. The device of claim 8, wherein the first material web has an underside and an upper side,
the first roller is for contacting the underside of the roller portion of the first material web,
the first breaking wing is for contacting the underside of the wing portion of the first material web,
the leading edge of the first folding portion is for contacting the underside of the wing portion of the first material web, and
the first folding portion is for folding the wing portion of the first material web onto the roller portion of the first material web such that the upper side of the wing portion of the first material web contacts the upper side of the roller portion of the first material web.

19. The device of claim 9, wherein the first roller and the first breaking wing are positioned relative to each other such that the roller portion of the first material web can have a different thickness than the wing portion of the first material web.

20. The device of claim 9, wherein the second material web and the first material web form one web in which the roller portion of the second material web is adjacent the roller portion of the first material web.

21. The device of claim 11, wherein the second rotational axis is the first rotational axis.

22. The device of claim 12, wherein the second roller and the first roller form one roller.

23. The device of claim 13, wherein the one roller has a low friction coating.

24. The device of claim 14, wherein the low-friction coating is Teflon impregnated with one of ceramic and cobalt.

25. The device of claim 13, wherein the first breaking wing further comprises a cooling jacket through which a cooling fluid flows to cool the first breaking wing.

26. The device of claim 16, wherein the first folding portion further comprises a cooling jacket through which a cooling fluid flows to cool the first folding portion.

27. A method of folding a first material web traveling in a machine direction, the method comprising:
feeding a roller portion of the first material web onto a first roller such that the roller portion of the first material web is supported by the first roller;
feeding a wing portion of the first material web onto a first breaking wing such that the wing portion of the first material web is supported by the first breaking wing; and
feeding the roller portion and the wing portion of the first material web to a first folding portion having a leading edge,
wherein the first breaking wing has a breaking edge,
the first roller is rotatably attached to the first breaking wing and has a surface and a first rotational axis along a first transverse direction, the first transverse direction being substantially perpendicular to the machine direction,
the surface of the first roller is positioned in the first transverse direction at a first angle relative to the first rotational axis,
the breaking edge of the first breaking wing is positioned in the transverse direction at a second angle relative to the first rotational axis, and
the first angle is different from the second angle.

28. The method of claim 27, wherein the roller portion of the first material web is to remain unfolded, and
the wing portion of the first material web is to be folded.

29. The method of claim 28, wherein the second angle is determined by calculating a preferred height which equals a thickness of the roller portion of the first material web multiplied by a reduced drag/material build-up factor.

30. The method of claim 29, wherein the second angle is such that the roller portion of the first material web remains in contact with the first roller and the wing portion of the first material web remains in contact with the first breaking wing.

31. The method of claim 30, wherein the leading edge of the first folding portion is set at a folding angle relative to the first rotational axis, and the folding angle is approximately 20 degrees.

32. The method of claim 27, wherein a web length of the wing portion of the first material web is approximately equal to a web length of the roller portion of the first material web.

33. The method of claim 27, wherein a web length of the wing portion of the first material web is substantially equal to a web length of the roller portion of the first material web.

34. The method of claim 27, wherein a web length of the wing portion of the first material web is equal to a web length of the roller portion of the first material web.

35. The method of claim 27, wherein the first material web has an underside and an upper side, the first roller contacts the underside of the roller portion of the first material web, the first breaking wing contacts the underside of the wing portion of the first material web, the leading edge of the first folding portion contacts the underside of the wing portion of the first material web, and the first folding portion folds the wing portion of the first material web onto the roller portion of the first material web such that the upper side of the wing portion of the first material web contacts the upper side of the roller portion of the first material web.

36. The method of claim 35, wherein the first roller and the first breaking wing are positioned relative to each other such that the roller portion of the first material web can have a different thickness than the wing portion of the first material web.

37. The method of claim 35, wherein the first breaking wing further comprises a cooling jacket through which a cooling fluid flows to cool the first breaking wing.

38. The method of claim 37, wherein the first folding portion further comprises a cooling jacket through which a cooling fluid flows to cool the first folding portion.

39. The method of claim 35, wherein the second material web and the first material web are different webs.

40. The method of claim 39, wherein the second rotational axis is the first rotational axis.

41. The method of claim 40, wherein the first breaking wing further comprises a cooling jacket through which a cooling fluid flows to cool the first breaking wing.

42. The method of claim 41, wherein the first folding portion further comprises a cooling jacket through which a cooling fluid flows to cool the first folding portion.

43. The method of claim 39, wherein the first breaking wing further comprises a cooling jacket through which a cooling fluid flows to cool the first breaking wing.

44. The method of claim 43, wherein the first folding portion further comprises a cooling jacket through which a cooling fluid flows to cool the first folding portion.

45. The method of claim 39, wherein the first roller and the first breaking wing are positioned relative to each other such that the roller portion of the first material web can have a different thickness than the wing portion of the first material web.

46. The method of claim 27, further comprising feeding a roller portion of a second material web onto a second roller such that the roller portion of the second material web is supported by the second roller;

feeding a wing portion of the second material web onto a second breaking wing such that the wing portion of the second material web is supported by the second breaking wing; and feeding the roller portion and the wing portion of the second material web to a second folding portion having a leading edge, wherein the second breaking wing has a breaking edge, the second roller is rotatably attached to the second breaking wing and has a surface and a second rotational axis along a second transverse direction, the second transverse direction being substantially perpendicular to the machine direction, the surface of the second roller is positioned in the second transverse direction at a third angle relative to the second rotational axis, the breaking edge of the second breaking wing is positioned in the second transverse direction at a fourth angle relative to the second rotational axis, and the third angle is different from the fourth angle.

47. The method of claim 46, wherein the first material web has an underside and an upper side, the first roller contacts the underside of the roller portion of the first material web, the first breaking wing contacts the underside of the wing portion of the first material web, the leading edge of the first folding portion contacts the underside of the wing portion of the first material web, and the first folding portion folds the wing portion of the first material web onto the roller portion of the first material web such that the upper side of the wing portion of the first material web contacts the upper side of the roller portion of the first material web.

48. The method of claim 47, wherein the first roller and the first breaking wing are positioned relative to each other such that the roller portion of the first material web can have a different thickness than the wing portion of the first material web.

49. The method of claim 47, wherein the second material web and the first material web form one web in which the roller portion of the second material web is adjacent the roller portion of the first material web.

50. The method of claim 49, wherein the second rotational axis is the first rotational axis.

51. The method of claim 50, wherein the second roller and the first roller form one roller.

52. The method of claim 51, wherein the one roller has a low friction coating.

53. The method of claim 52, wherein the low-friction coating is Teflon impregnated with one of ceramic and cobalt.

54. The method of claim 51, wherein the first breaking wing further comprises a cooling jacket through which a cooling fluid flows to cool the first breaking wing.

55. The method of claim 54, wherein the first folding portion further comprises a cooling jacket through which a cooling fluid flows to cool the first folding portion.

* * * * *